United States Patent
Dill et al.

(10) Patent No.: US 10,852,261 B2
(45) Date of Patent: Dec. 1, 2020

(54) SENSOR AND METHOD FOR MEASURING RESPIRATORY GAS PROPERTIES

(71) Applicant: Sendsor GmbH, Munich (DE)

(72) Inventors: Dieter Helmut Dill, Munich (DE); Matthias Maurberger, Munich (DE); Alexander Scholz, Bischofswiesen (DE)

(73) Assignee: Sendsor GmbH, Munich (DE)

(*) Notice: Subject to any disclaimer, the term of this patent is extended or adjusted under 35 U.S.C. 154(b) by 468 days.

(21) Appl. No.: 15/638,484

(22) Filed: Jun. 30, 2017

(65) Prior Publication Data

US 2018/0120245 A1    May 3, 2018

Related U.S. Application Data

(60) Provisional application No. 62/414,668, filed on Oct. 29, 2016.

(51) Int. Cl.
| | |
|---|---|
| *G01N 25/18* | (2006.01) |
| *G01N 21/84* | (2006.01) |
| *G01J 5/08* | (2006.01) |
| *A61B 5/01* | (2006.01) |
| *A61B 5/08* | (2006.01) |
| *G01N 25/72* | (2006.01) |
| *A61B 5/00* | (2006.01) |

(52) U.S. Cl.
CPC ........... *G01N 25/18* (2013.01); *A61B 5/01* (2013.01); *A61B 5/082* (2013.01); *G01J 5/0853* (2013.01); *G01N 21/8422* (2013.01); *A61B 5/00* (2013.01); *G01N 25/72* (2013.01)

(58) Field of Classification Search
CPC ........ G01N 25/18; G01N 25/40; G01N 25/42; G01N 25/48–4893; G01N 27/18
See application file for complete search history.

(56) References Cited

U.S. PATENT DOCUMENTS

| | | | | |
|---|---|---|---|---|
| 3,720,093 | A * | 3/1973 | Gill | G01N 27/185 73/25.03 |
| 3,910,261 | A * | 10/1975 | Ragsdale | A61B 5/0836 600/532 |
| 3,913,379 | A * | 10/1975 | Rusz | A61B 5/087 73/23.21 |

(Continued)

FOREIGN PATENT DOCUMENTS

JP        2010236972 A  * 10/2010

OTHER PUBLICATIONS

English Translation of JP 2010-236972, Oct. 2010.*

(Continued)

*Primary Examiner* — Alexander A Mercado
(74) *Attorney, Agent, or Firm* — Smartpat PLC

(57) ABSTRACT

A sensor and method for measuring respiratory gas properties are presented. A thermal conductivity sensor is used to measure the thermal conductivity of a gas with unknown composition and/or mass flow rate at different temperatures. The measured thermal conductivities at different temperatures are compared with known thermal conductivities of gases at different temperatures. In an exemplary application the sensor and method are installed in a tube to determine a mass of respiratory air flowing through the tube and a concentration of $CO_2$ therein.

19 Claims, 7 Drawing Sheets

(56) References Cited

U.S. PATENT DOCUMENTS

| | | | | |
|---|---|---|---|---|
| 4,944,035 A | * | 7/1990 | Aagardl | G01N 25/005 374/30 |
| 4,956,793 A | * | 9/1990 | Bonne | G01N 9/04 374/43 |
| 5,094,246 A | * | 3/1992 | Rusz | A61B 5/0816 128/205.23 |
| 6,763,711 B1 | | 7/2004 | Nair et al. | |
| 6,843,100 B2 | | 1/2005 | Bair et al. | |
| 8,636,956 B2 | | 1/2014 | Yamamori et al. | |
| 8,696,588 B2 | | 4/2014 | Hansmann et al. | |
| 8,753,286 B2 | | 6/2014 | Scholz | |
| 9,335,307 B2 | | 5/2016 | Wang et al. | |
| 2002/0185129 A1 | * | 12/2002 | Fisher | A61B 5/0836 128/203.25 |
| 2002/0190054 A1 | * | 12/2002 | Ito | H05B 3/265 219/444.1 |
| 2003/0041650 A1 | * | 3/2003 | Dimarzo | G01N 25/18 73/25.01 |
| 2003/0119197 A1 | * | 6/2003 | Bonne | G01N 27/18 436/149 |
| 2004/0087867 A1 | * | 5/2004 | Gama De Abreu | A61B 5/029 600/529 |
| 2004/0206747 A1 | * | 10/2004 | Ito | H01L 21/67109 219/468.1 |
| 2005/0025215 A1 | * | 2/2005 | Arndt | G01N 25/18 374/44 |
| 2005/0034533 A1 | * | 2/2005 | Wang | G01F 1/708 73/861.05 |
| 2005/0049805 A1 | * | 3/2005 | Bonne | G01N 27/185 702/57 |
| 2005/0265422 A1 | * | 12/2005 | Bonne | G01N 30/66 374/44 |
| 2006/0010987 A1 | * | 1/2006 | Fraser | G01F 1/708 73/861.07 |
| 2006/0169024 A1 | * | 8/2006 | Shoji | H01M 8/04126 73/23.2 |
| 2006/0199135 A1 | * | 9/2006 | Mashima | H01L 21/67109 432/214 |
| 2006/0260610 A1 | * | 11/2006 | Matthiessen | A62B 7/02 128/203.15 |
| 2007/0006639 A1 | * | 1/2007 | Sasanuma | G01N 25/18 73/53.01 |
| 2007/0062531 A1 | * | 3/2007 | Fisher | A61B 5/083 128/204.23 |
| 2007/0240718 A1 | * | 10/2007 | Daly | A61M 16/0045 128/204.22 |
| 2009/0164163 A1 | * | 6/2009 | Wang | G01F 1/6965 702/100 |
| 2009/0272656 A1 | * | 11/2009 | Varney | A61B 5/0836 205/785.5 |
| 2009/0277246 A1 | * | 11/2009 | Ooishi | G01N 33/225 73/25.03 |
| 2010/0050735 A1 | * | 3/2010 | Varney | A61B 5/0836 73/23.3 |
| 2010/0139659 A1 | * | 6/2010 | Von Blumenthal | A61M 16/0051 128/204.23 |
| 2011/0077872 A1 | * | 3/2011 | Loui | G01N 29/036 702/24 |
| 2011/0154885 A1 | * | 6/2011 | Nakano | G01N 25/18 73/25.03 |
| 2012/0024043 A1 | * | 2/2012 | McBrady | G01N 30/66 73/25.03 |
| 2012/0226180 A1 | | 9/2012 | Volkel et al. | |
| 2013/0065146 A1 | * | 3/2013 | Ooishi | G01N 33/225 429/427 |
| 2014/0016664 A1 | * | 1/2014 | Pauchet | G01N 25/18 374/44 |
| 2014/0373621 A1 | * | 12/2014 | Schirm | G01F 1/6965 73/204.11 |
| 2015/0052974 A1 | * | 2/2015 | Pieczarek | G01N 25/18 73/25.03 |
| 2015/0068299 A1 | * | 3/2015 | Zhu | H05K 3/46 73/204.23 |
| 2015/0075256 A1 | * | 3/2015 | Basham | G01N 33/0062 73/31.01 |
| 2016/0025694 A1 | * | 1/2016 | Brandau | G01N 27/185 73/25.03 |
| 2016/0033433 A1 | * | 2/2016 | Nakano | G01N 33/005 73/25.01 |
| 2017/0030873 A1 | * | 2/2017 | Gellert | B01L 3/5027 |
| 2017/0069821 A1 | * | 3/2017 | Mouri | H01L 41/0973 |
| 2017/0363589 A1 | * | 12/2017 | Kumar | G01N 25/18 |
| 2018/0052124 A1 | * | 2/2018 | Rogers | G01N 25/18 |
| 2018/0087815 A1 | * | 3/2018 | Kujak | G01N 25/18 |
| 2018/0168225 A1 | * | 6/2018 | Zinovik | A24F 47/008 |
| 2018/0180455 A1 | * | 6/2018 | Nakao | G01N 25/18 |
| 2018/0235030 A1 | * | 8/2018 | Tyler | B33Y 30/00 |
| 2018/0292336 A1 | * | 10/2018 | Ottosen | B01D 53/0407 |
| 2018/0296158 A1 | * | 10/2018 | Fisher | A61M 16/206 |
| 2018/0313800 A1 | * | 11/2018 | Rogers | G01N 25/48 |
| 2019/0060591 A1 | * | 2/2019 | Kertser | A61M 16/0841 |
| 2019/0120821 A1 | * | 4/2019 | Atsalakis | A61B 5/087 |
| 2019/0293590 A1 | * | 9/2019 | Merz | H05B 3/22 |
| 2020/0049681 A1 | * | 2/2020 | Ludwig | G01N 33/0073 |

OTHER PUBLICATIONS

Loui, A., et al. "Detection and discrimination of pure gases and binary mixtures using a dual-modality microcantilever sensor." Sensors and Actuators A: Physical 159.1 (2010): 58-63. (Year: 2010).*

* cited by examiner

SENSOR AND METHOD FOR MEASURING RESPIRATORY GAS PROPERTIES

TECHNICAL FIELD

The present disclosure generally relates to a sensor and method for measuring gas properties, and more particularly, to a respiratory gas sensing system and method for measuring the concentration of carbon dioxide in a respiratory gas.

BACKGROUND

In the medical field, various diagnostic and therapeutic devices require an analysis of gases within the air that is inhaled and/or exhaled by a patient. Such devices include spiroergometers, breathing trainers, respirators, and anesthesia machines. Due to high complexity and cost of such devices their use is usually limited to medical applications or niche applications such as performance diagnostics in professional sports.

Spirometry is the most common of the pulmonary function tests (PFTs), measuring lung function, specifically the amount (volume) and/or speed (flow) of air that can be inhaled and exhaled. Spirometry is an important tool used for generating pneumotachographs, which are helpful in assessing conditions such as asthma, pulmonary fibrosis, and cystic fibrosis, and COPD.

Spirometers are known which use differential pressure sensors, ultrasonic sensors, turbine wheel sensors and hot-wire anemometers. An exemplary spirometer with replaceable flow tube is disclosed in U.S. Pat. No. 8,753,286 which is incorporated by reference in its entirety.

A precise and direct method for determining metabolic activity in humans is the analysis of the respiratory gases, in which the concentration of oxygen and carbon dioxide in the breath as well as the volume flow of the breath are determined. Metabolic values such as, for example, the respiratory quotient (RQ) can be calculated on the basis of the measurements. RQ is the ratio of the amount of exhaled carbon dioxide to the amount of oxygen taken in. To determine these gas quantities, various parameters are measured. The flow volume of the respiratory gas is determined using a sensor which measures the flow velocity of the respiratory gas by measuring the ultrasound travel time, for example. Various respiratory volumes can be derived through the integration of the volume flow over time. In known spiroergometry (or ergospirometry) devices, a gas sample is also suctioned off from the main respiratory flow and fed to the sensor system contained in the device. The sensor system typically contain chemical analysis sensors. As a result, the concentrations of oxygen and carbon dioxide upon inhaling and exhaling can be determined. The respective values of the gas concentrations differ substantially between inhaling and exhaling. Using the previously determined respiratory volume, the gas quantities that were converted by the body can be calculated from the concentrations. An exemplary user unit for determining output parameters from breath gas analyses is disclosed in U.S. patent application publication US2012/0226180 which is hereby incorporated by reference.

A problem with conventional devices is that they are rather large, expensive, and energy-consuming, making them not suitable for battery-powered, mobile use.

SUMMARY

A respiratory gas sensing system is presented. The sensor uses a thermal conductivity sensor which is disposed within a respiratory flow path. A processing module is operatively connected to the thermal conductivity sensor. The processing module measures a first thermal conductivity of the respiratory gas at a first temperature and measures a second thermal conductivity of the respiratory gas at a second temperature. The second temperature is higher than the first temperature. The processing module then determines a concentration of carbon dioxide within the respiratory gas in response to the measured first thermal conductivity and the measured second thermal conductivity. The processing module may use additional inputs in determining the concentration of carbon dioxide beyond the measured first and second thermal conductivity.

The thermal conductivity sensor may include a first thermal conductivity sensing element and a second thermal conductivity sensing element. In that case, the processing module may be configured to operate the first thermal conductivity sensing element at the first temperature and to operate the second thermal conductivity sensing element at the second temperature.

The respiratory gas sensing system may be arranged within a tube through which the respiratory gas flows such that the first thermal conductivity sensing element and the second thermal conductivity sensing element are arranged in a plane substantially parallel to a longitudinal extension of the tube. This arrangement is advantageous if thermal crosstalk between the first and the second thermal conductivity sensing element is desired. That may be the case to reduce the overall energy required to heat the first and the second thermal sensing element due to their arrangement in which heating one sensing element affects the temperature of the other sensing element.

Alternatively, the first thermal conductivity sensing element and the second thermal conductivity sensing element may be arranged in a plane substantially perpendicular to a longitudinal extension of the tube. That arrangement may be preferred to reduce thermal cross-talk between the sensing elements.

The thermal conductivity sensing element may be a meander-shaped resistive wire forming part of an analog or digital measuring circuit. The measuring circuit may e.g. utilize a Wheatstone bridge. If two thermal conductivity sensing elements are used the first sensing element may be part of a measuring circuit (e.g. a first Wheatstone bridge) and the second sensing element may be part of a second measuring circuit (e.g. a second Wheatstone bridge).

The first and the second thermal conductivity sensing elements may be arranged in close proximity to one another. In particular, the thermal conductivity sensing elements may be arranged on a membrane within an area of less than 4 $mm^2$.

As described, the respiratory gas sensing system may use two different thermal conductivity sensing elements which operate simultaneously at two different temperatures. Alternatively, the respiratory gas sensing system may use a single thermal conductivity sensor which operates, over time, at two or more different temperatures. More specifically, the processing module may be configured to alternately operate the thermal conductivity sensing element at the first temperature and at the second temperature. If the thermal conductivity sensing element is part of a Wheatstone bridge the different temperatures of the thermal conductivity sensing element may be affected by selectively changing a resistor value of a resistor in the Wheatstone bridge.

Within a larger device the respiratory gas sensing system may be arranged within a longitudinally elongated tube through which respiratory gas flows. The tube may have a proximal end and a distal end. The proximal end may be connected to a breathing mask which can be worn by a subject. In such a configuration a first temperature sensing element may be provided laterally spaced apart from the thermal conductivity sensor on either the proximal or the distal side of the thermal conductivity sensing element. Alternatively, two temperature sensing elements may be provided, one arranged on a proximal side of the thermal conductivity sensor and a second temperature sensing element arranged on a distal side of the thermal conductivity sensor.

The sensor may use a have first temperature of less than 200° C. and a second temperature of more than 200° C.

Measuring the thermal conductivity of a respiratory gas at two different temperatures may be sufficient to determine the concentration of $CO_2$ therein, even if the humidity and/or flow of the respiratory gas is unknown. However, more accurate determination of $CO_2$ concentration may be accomplished by using measurements at more than two different temperatures. For example, the respiratory gas sensing system may measure the thermal conductivity of a respiratory gas at three different temperatures and determine the concentration of carbon dioxide within the respiratory gas in response to all three measured thermal conductivities. In particular, the respiratory gas sensing system may operate at a first temperature which is less than 150° C., a second temperature between 150° C. and 250° C., and a third temperature of more than 250° C.

To operate simultaneously at three different temperatures the thermal conductivity sensor may comprise a first thermal conductivity sensing element, a second thermal conductivity sensing element, and a third thermal conductivity sensing element. The processing module may then be configured to operate the first thermal conductivity sensing element at the first temperature, to operate the second thermal conductivity sensing element at the second temperature, and to operate the third thermal conductivity sensing element at the third temperature. Structurally, the third thermal conductivity sensing element may be arranged centrally between the first thermal conductivity sensing element and the second thermal conductivity sensing, i.e. the hottest thermal conductivity sensing element may be arranged in between two thermal conductivity sensing elements which operate at lower temperatures.

Alternatively, the sensor may utilize pairs of sensing elements that operate at the same temperature. For example, the thermal conductivity sensor may use two outer thermal conductivity sensing elements, two inner thermal conductivity sensing elements and one central thermal conductivity sensing element. The sensor in that case may have a symmetrical structure in which the two inner thermal conductivity sensing elements are arranged inwardly of the two outer thermal conductivity sensing elements and the central thermal conductivity sensing element is arranged between the two inner thermal conductivity sensing elements. In that configuration the two outer thermal conductivity sensing elements may operate at the first temperature and the inner thermal conductivity sensing element may operate at the second temperature. The central thermal conductivity sensing element may operate at a third temperature which is higher than the second temperature.

The respiratory gas sensing system may operate at absolute temperatures. That is, the first temperature and the second temperature may be predetermined absolute temperatures. Alternatively, the respiratory gas sensing system may operate at relative temperatures above ambient temperature or above a temperature of the respiratory gas.

The sensor as described above may be utilized in various devices, and may in particular be used in medical applications. For example, the sensor may be used within a spiroergometer having a tube with a proximal end and a distal end. A breathing mask may be connected to the proximal end of the tube and the sensor may be arranged within the tube. The compact form and low power consumption of the disclosed respiratory gas sensing system enables spiroergometers in which the breathing mask and the sensor are formed as a portable, battery powered device which is worn by a subject while exercising.

To improve measurement accuracy it may be desirable to measure the carbon dioxide concentration in the respiratory gas while it is not moving. This may be accomplished by providing a spiroergometer in which the tube comprises a first branch and a second branch. A trap section for exhaled respiratory gas may be formed between two flow control valves in the second branch, and the respiratory gas sensing system may utilize a thermal conductivity sensor arranged within the trap section of the second branch.

A respiratory flow control system may have a tube having a proximal end and a distal end. A breathing mask may be connected to the proximal end of the tube and be worn by a subject. A thermal conductivity sensor may be arranged within the tube. The tube may comprise a first branch and a second branch. A flow of respiratory gas through the first branch may be controlled by a first flow control valve arranged within the first branch. A flow of respiratory gas through the second branch may be controlled by a second flow control valve arranged within the second branch. The first flow control valve and the second flow control valve may be controlled by the processing module in response to the concentration of carbon dioxide determined by the processing module.

For anesthetic applications such a respiratory flow control system may be used in a configuration where the tube comprises a first branch having an open distal end and a second branch having a distal end connected to a reservoir comprising an anesthetic gas.

The respiratory flow control system may determine a respiratory volume flow in response to measuring a respiratory mass flow and the concentration of carbon dioxide. A method for analyzing a respiratory gas may be based on providing a thermal conductivity sensor within a respiratory flow path. The method may then use the steps of measuring a first thermal conductivity of the respiratory gas at a first temperature and measuring a second thermal conductivity of the respiratory gas at a second temperature. Finally, the method may determine a concentration of carbon dioxide within the respiratory gas in response to the measured first thermal conductivity and the measured second thermal conductivity. Determining the concentration of carbon dioxide may in particular be based on comparing the measurements with data contained within a look-up table. Determining the concentration of carbon dioxide within the respiratory gas may thus comprise comparing the first measured thermal conductivity and the second measured conductivity with known thermal conductivities of gases at different temperatures.

For improved measurement accuracy the thermal conductivity sensor may be provided within a trap for exhaled air and the first thermal conductivity and the second thermal conductivity may be measured while exhaled air is trapped, i.e. while the exhaled air is not flowing.

More generically, a method for measuring a property of a mixture of gases is presented. The method includes providing one or more thermal conductivity sensing elements within the mixture of gases. Heating power is applied to one of the one or more thermal conductivity sensing elements and controlled to maintain a selected first temperature. A first voltage and/or first power required to maintain the first temperature is measured. Further, heating power is applied to one of the one or more thermal conductivity sensing elements and controlled to maintain a selected second temperature. A second voltage and/or second power required to maintain the second temperature is measured. The concentration of at least one gas contained in the mixture of gases is determined in response to the measured first voltage and/or first power and the measured second voltage and/or second power.

The following detailed description of the invention is merely exemplary in nature and is not intended to limit the invention or the application and uses of the invention. Furthermore, there is no intention to be bound by any theory presented in the preceding background of the invention or the following detailed description of the invention.

DETAILED DESCRIPTION

Figure 1:
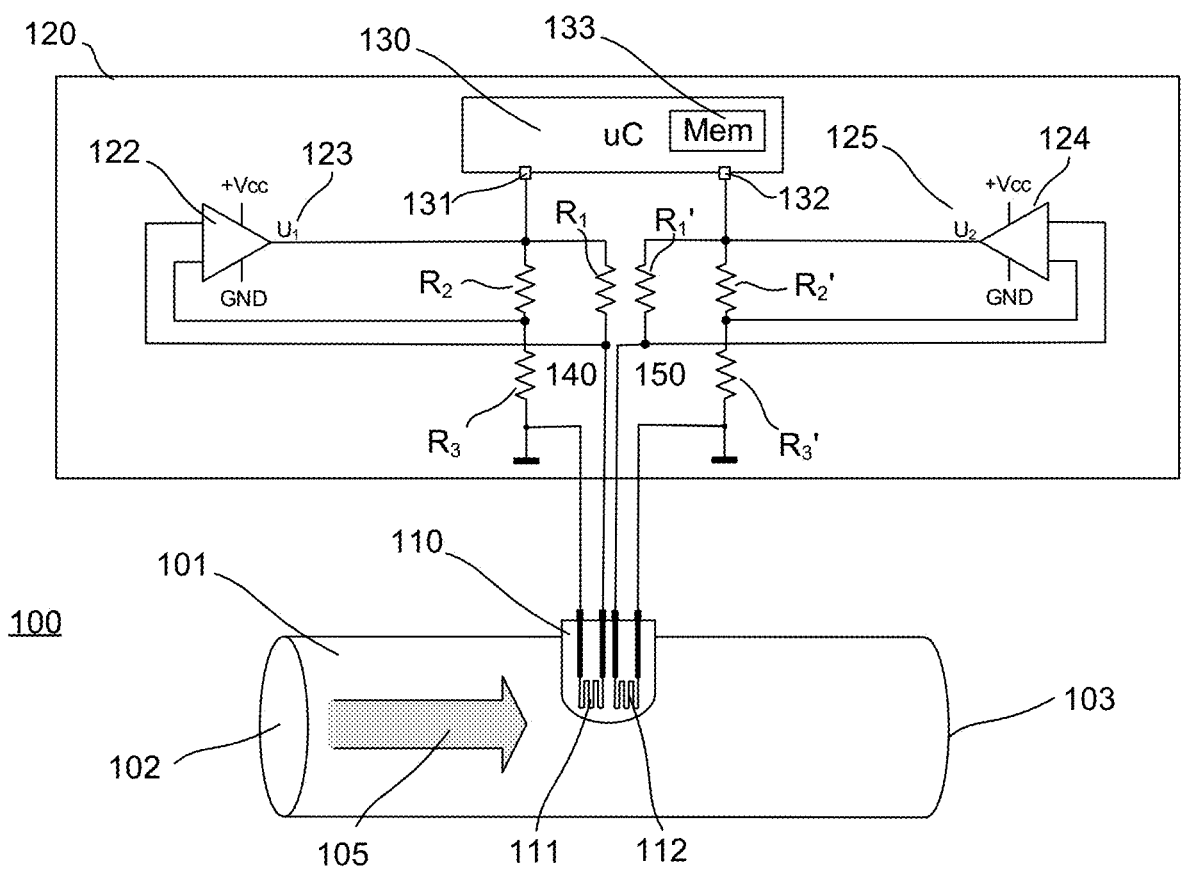
FIG. 1 is a schematic illustration of an exemplary respiratory gas sensing system.

An exemplary respiratory gas sensing system 100 is schematically illustrated in FIG. 1. The sensing system 100 uses a thermal conductivity sensor 110 which is arranged within a tube 101 through which a subject inhales and/or exhales. The tube 101 establishes a respiratory flow path 105 from a proximal end 102 to a distal end 103 of tube 101. The tube 101 may carry only a portion of the respiratory gas inhaled and/or exhaled by the subject. A processing module 120 is operatively connected to the thermal conductivity sensor 110. The processing module 120 measures a first thermal conductivity of the respiratory gas present within the tube 101 at a first temperature and a second thermal conductivity of the respiratory gas at a second, higher temperature. The processing module then determines a concentration of carbon dioxide within the respiratory gas in response to the measured first thermal conductivity and the measured second thermal conductivity. The processing module may use a processor 130 having an internal memory 133 to perform the determination of carbon dioxide concentration.

The thermal conductivity sensor 110 may have a first thermal conductivity sensing element 111 which operates at the first temperature and a second thermal conductivity sensing element 112 which operates at the second temperature. The thermal conductivity sensing elements may be electrically connected within electronic measuring circuits. The electronic measuring circuits are configured to generate an output signal which changes with the thermal conductivity of the air surrounding the sensing elements 111,112. The sensing elements 111,112 are PTC elements, that is they have a positive temperature coefficient of resistance. Various forms of electronic measuring circuits are known to be used to evaluate the resistance of a PTC element and may be used in combination with the sensing elements 111,112.

One exemplary electronic measuring circuit is a Wheatstone bridge circuit. As shown in FIG. 1, the first thermal conductivity sensing element 111 is part of a first Wheatstone bridge 140. The first thermal conductivity sensing element 111 may be a meander-shaped resistive wire which is electrically connected in series with a first resistor $R_1$. The first resistor $R_1$ and the first thermal conductivity sensing element are wired in parallel to a second resistor $R_2$ and a third resistor $R_3$, jointly forming the Wheatstone bridge 140. The voltage across the Wheatstone bridge 140 forms the input of a first amplifier 122. The output of the first amplifier 123 powers the Wheatstone bridge 140.

The first amplifier 122 may be an operational amplifier having a high amplification factor. In that case the amplifier's output voltage $U_1$ will assume a steady state when its input is essentially zero, i.e. when the voltage across the Wheatstone bridge is essentially zero. This is the case when $$\frac{R_2}{R_3} = \frac{R_1}{R_{111}}$$

with $R_{111}$ being the resistance of the first thermal conductivity sensing element 111. The resistance of the first thermal conductivity sensing element 111 is temperature-dependent and may increase with temperature.

$$R_{111} = f(T_{111})$$

With $T_{111}$ being the temperature of the first thermal conductivity sensing element 111.

The voltage across the first Wheatstone bridge 140 thus becomes zero when the first thermal conductivity sensing element 111 assumes a Temperature $T_{111}$ so that $$\frac{R_2}{R_3} = \frac{R_1}{f(T_{111})}$$

The power needed to heat the first thermal conductivity sensing element 111 to its first operating temperature $T_{111}$ depends on the thermal conductivity of the respiratory gas surrounding the sensing element 111. Consequently, the output voltage $U_1$ of the first amplifier 122 is a measure of the thermal conductivity of the respiratory gas surrounding the first thermal conductivity sensing element 111. The output of the first amplifier 123 is operatively connected to a first A/D input 131 of a processor 130 which determines of the concentration of carbon dioxide within the respiratory gas.

The second thermal conductivity sensing element 112 is electrically connected within a second Wheatstone bridge 150. In particular, the second thermal conductivity sensing element 112 is connected in series with a fourth resistor $R_1'$. The second thermal conductivity sensing element 112 and the fourth resistor $R_1'$ are connected parallel to a fifth resistor $R_2'$ and a sixth resistor $R_3'$. The voltage across the second Wheatstone bridge 150 provides an input for a second amplifier 124. The output of the second amplifier 125 powers the second Wheatstone bridge 150 and is operatively connected to a second A/D input 132 of the processor 130. The resistor values of $R_1'$, $R_2'$, $R_3'$ are selected such that the second thermal conductivity sensing element 112 operates at the second temperature $T_{112}$.

The processor 130 may be an integrated microcontroller. The processor 130 may read (sensor) inputs, control outputs, manage sensor signals, interpret the signals as computer data, communicate with other control systems and remote computer systems, receive user input, and instruct actuators to control flow control valves, as described below.

The processor 130 may run computer programs that may comprise ordered listings of executable instructions for implementing logical functions. The computer programs may be stored in or on computer-readable medium 133 residing on or accessible by the processor 130. The computer programs can be embodied in any computer-readable medium for use by or in connection with an instruction execution system, apparatus, or device, such as a computer-based system, processor-containing system, or other system that can fetch the instructions from the instruction execution system, apparatus, or device, and execute the instructions. In the context of this document, a "computer-readable medium" can be any means that can contain, store, communicate, propagate or transport the program for use by or in connection with the instruction execution system, apparatus, or device. The computer-readable medium can be, for example, but is not limited to, an electronic, magnetic, optical, electromagnetic, infrared, or semi-conductor system, apparatus, device, or propagation medium. More specific, although not inclusive, examples of the computer-readable medium would include the following: an electrical connection having one or more wires, a portable computer diskette, a random access memory (RAM), a read-only memory (ROM), an erasable, programmable, read-only memory (EPROM or Flash memory), an optical fiber, and a portable compact disk read-only memory (CDROM).

The respiratory gas sensing system 100 as shown in FIG. 1 uses a thermal conductivity sensor 110 with two thermal conductivity sensing elements 111,112. The respiratory gas sensing system 100 can simultaneously determine the thermal conductivity of the respiratory gas at two different temperatures. In some applications it may suffice to determine the thermal conductivity of the respiratory gas sequentially at two different temperatures. An exemplary such system is shown in FIG. 2.

Figure 2:
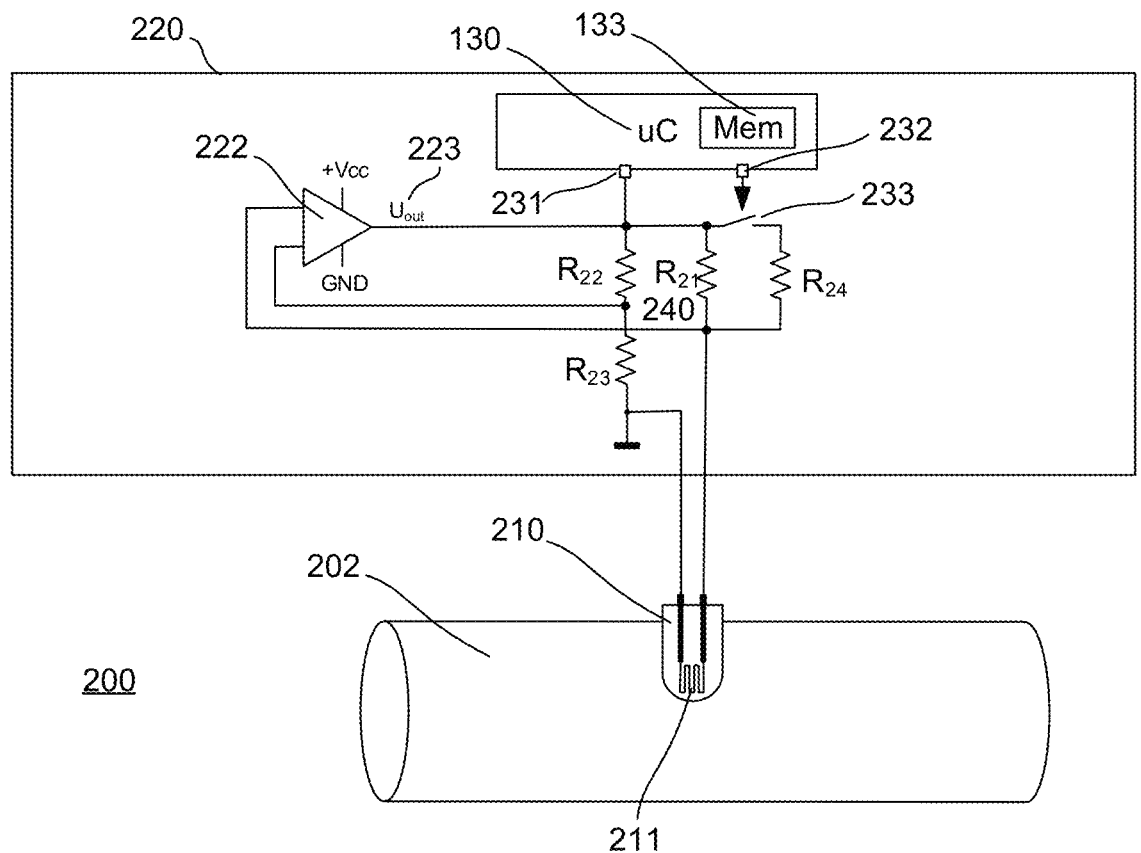
FIG. 2 is a schematic illustration of an alternative exemplary respiratory gas sensing system.

The respiratory gas sensing system 200 shown in FIG. 2 uses a thermal conductivity sensor 210 which contains a single thermal conductivity sensing element 211. The thermal conductivity sensor 210 is arranged in a tube 202 which is filled with a respiratory gas so that the thermal conductivity sensor 210 is surrounded by the respiratory gas that is to be analyzed. The thermal conductivity sensing element 211 may be a meander shaped resistive wire with a positive temperature coefficient (PTC). That it, the thermal conductivity sensing element 211 may be made of a material that experiences an increase in electrical resistance when its temperature is raised.

The thermal conductivity sensing element 211 is connected to a measuring circuit, e.g. a Wheatstone bridge 240. The Wheatstone bridge 240 may be formed by a first resistor $R_{21}$ in series with the thermal conductivity sensing element 211 and a second resistor $R_{22}$ and third resistor $R_{23}$ in parallel to the first resistor $R_{21}$ and the sensing element 211.

The Wheatstone bridge 240 may be powered by the output 223 of an amplifier 222. The amplifier 222 may amplify the voltage across the Wheatstone bridge 240. The output voltage $U_{out}$ may be read in processor 130 through and A/D input 231.

To operate the thermal conductivity sensing element 211 at different temperatures at least one of the Wheatstone bridge resistors $R_{21}$, $R_{22}$, $R_{23}$ may be adjustable. For example, a fourth resistor $R_{24}$ may be provided and selectively connected by a relay 233 in parallel to the first resistor $R_{21}$. By connecting a fourth resistor $R_{24}$ in parallel to the first resistor $R_{21}$ the overall resistance which is in series with the thermal conductivity sensing element decreases and the voltage across the bridge changes. This ultimately leads to a change in the output voltage $U_{out}$ of the amplifier 222 and a corresponding change in the temperature $T_2$ at which the thermal conductivity sensing element 211 operates. The relay 233 may be controlled by the processor 130 through an output 232.

The processor 130 may selectively open and close the relay 233 and thereby operate the thermal conductivity sensing element at a first temperature $T_1$ when the relay 233 is open and at a second temperature $T_2$ when the relay 233 is closed. The processor 130 may evaluate the output voltage $U_{out}$ to determine the thermal conductivity of the respiratory gas surrounding the thermal conductivity sensing element 211 and ultimately determine the concentration of carbon dioxide therein by comparing the thermal conductivity of the respiratory gas at the first temperature $T_1$ with its thermal conductivity at the second temperature $T_2$.

Figure 3:
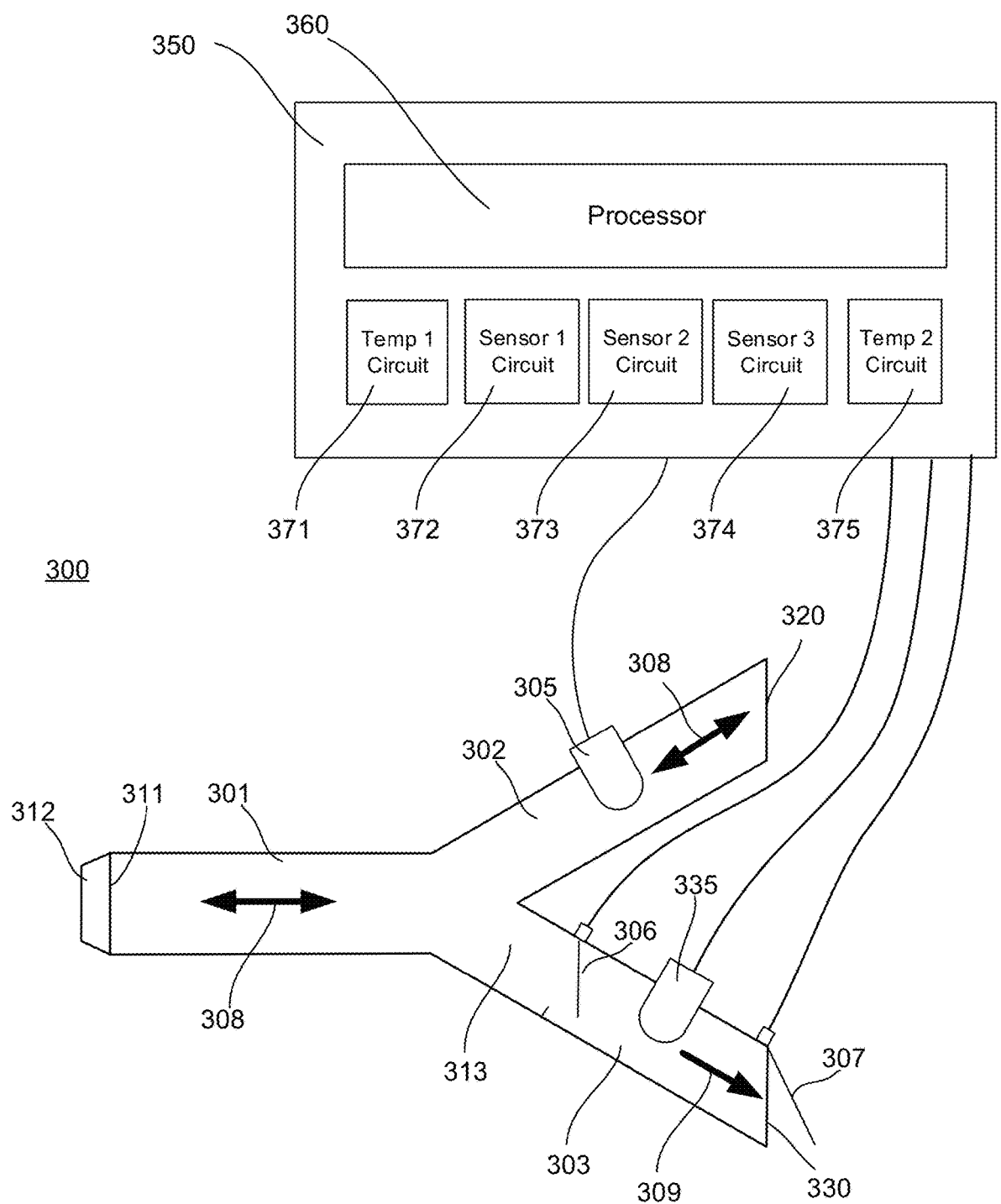
FIG. 3 is a schematic illustration of an exemplary spiroergometer.

An exemplary spiroergometer 300 which uses a respiratory gas sensing system is schematically shown in FIG. 3. The spiroergometer 300 has a tube 301 having a proximal end 311. When in use, the proximal end 311 of the tube 301 may be connected to a breathing mask 312 which covers a subject's mouth and/or nose. The tube 301 has at least one distal end 320. At least one thermal conductivity sensor 305 is provided within the tube 301. The thermal conductivity sensor 305 is operatively connected to a processing module 350.

As illustrated, the tube 301 may split into a first branch 302 having a first distal end 320 and a second branch 303 having a second distal end 330. In this configuration, a first thermal conductivity sensor 305 may be provided in the first branch 302 of the tube 301 and a second thermal conductivity sensor 335 may be provided in the second branch 303 of the tube 301. The second thermal conductivity sensor 335 may be operatively connected to the processing module 350.

Within the second branch 303 of the tube 301 one of more flaps 306,307 may be provided to seal the second branch 303 and prevent air from flowing through the second branch 303. The one or more flaps 306,307 may include an entry flap 306 arranged close to a proximal end 313 of the second branch 303 where the tube 301 splits into the first branch 302 and the second branch 303. Additionally or alternatively, an exit flap 307 may be provided close to the distal end 330 of the second branch. The section of the second branch between the entry flap 306 and the exit flap 307 may form a trap for exhaled air: When both the entry flap 306 and the exit flap 307 are closed while a subject is inhaling through the first branch 302 the previously exhaled air is trapped in the second branch 303 and can be analyzed while the exhaled air not moving.

The tube 301, including its first branch 302 and second branch 303, define a respiratory flow path. Respiratory gas flows through the tube 301 when a subject is inhaling and exhaling. The flaps 306,307 in the second branch 303 may be passive and form a one-way valve. For example, the flaps 306,307 may open only when air is exhaled through the tube 301, i.e. when air flows from the proximal end 311 to the distal ends 320, 330. The unidirectional flow of air through the second branch 303 is illustrated by the one-directional arrow 309 in the second branch 303. As illustrated, no flaps are provided in the first branch 302 of the tube 301, allowing air to flow bidirectionally between the proximal end 311 of the tube 301 and the distal end 320 of the first branch 302. The bidirectional flow of the respiratory gas is illustrated by arrows 308.

Alternatively, flaps 306, 307 may be actively controlled between an open state and a closed state. In an active control configuration the entry flap 306 and/or the exit flap 307 may be operatively connected to the processing module 350. Whether actively controlled or passive, the flaps 306,307 may be referred to as flow control valves.

Figure 4:
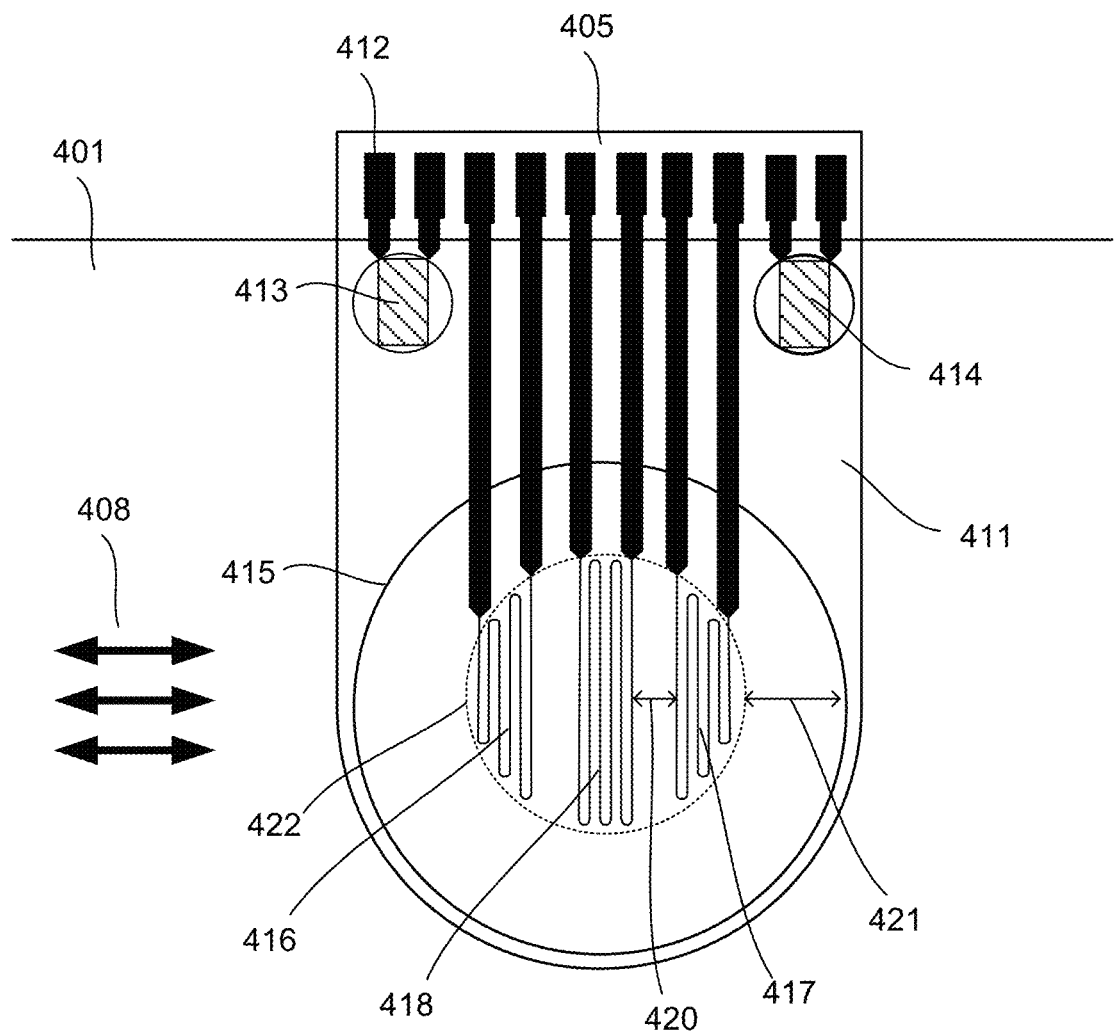
FIG. 4 is a detailed schematic view of a thermal conductivity sensor.

FIG. 4 shows a more detailed schematic view of a thermal conductivity sensor 405 which may be used in the configuration as in FIG. 3. The thermal conductivity sensor 405 is arranged inside a tube 401 and exposed to a respiratory gas 408 which is present in or flowing through the tube 401. The sensor 405 contains a first temperature sensing element 413 which may be electrically connected to a first temperature sensing circuit 371 within the processing module 350. The sensor 405 further contains a second temperature sensing element 414 which may be electrically connected to a second temperature sensing circuit 375 within the processing module 350. The temperature sensing circuits 371,375 may comprise A/D conversion components and power supply components, e.g. a pull-up resistor and a measuring shunt. The temperature sensing circuits 371,375 are operatively connected to the processor 360 within the processing module 350. The temperature sensing elements 413, 414 may be arranged within the flow of respiratory air 408 in the tube 401 inwardly of and radially spaced apart from thermal conductivity sensing elements 416,417,418. This arrangement provides that the temperature sensing elements 413, 414 can measure the temperature of respiratory air 408 flowing through the tube 401 without being affected by the actively heated thermal conductivity sensing elements 416, 417, 418. Furthermore, the first temperature sensing element 413 may be arranged longitudinally spaced apart from the second temperature sensing element 414 with the thermal conductivity sensing elements 416,417,418 arranged in between. This arrangement guarantees that one temperature sensing element is arranged upstream and one temperature sensing element is arranged downstream of the thermal conductivity sensing elements 416,417,418 regardless of the direction of airflow 408 through the tube 401.

The sensor 405 uses one or more thermal conductivity sensing elements 416,417,418. The thermal conductivity sensing elements 416,417,418 may be arranged within a common plane, substantially parallel to the flow of respiratory air 408 in the tube 401. Alternatively, the thermal conductivity sensing elements 416,417,418 may be arranged in a plane substantially perpendicular to the flow of air 408 in the tube 401. "Substantially parallel" should be understood to mean within 20 degrees, and more preferably within 10 degrees of being parallel. "Substantially perpendicular" should be understood to mean within 20 degrees of being perpendicular, and more preferably within 10 degrees of being perpendicular.

The thermal conductivity sensing elements 416,417,418 may be meander-shaped resistive wires and operate as hot-wire anemometers. The thermal conductivity sensing elements 416,417,418 may be made of nickel, platinum, molybdenum or tungsten. Use of another material with a high linear resistance temperature coefficient is possible. The thermal conductivity sensing elements 416,417,418 may be made of the same or different materials. Advantageously, the thermal conductivity sensing elements 416,417, 418 are small and arranged close together, e.g. within an area of 4 $mm^2$ to reduce power consumption and improve dynamic behavior.

The thermal conductivity sensing elements 416,417,418 may be heated to a predetermined temperature by applying power to the sensing elements. More specifically, a variable voltage may be generated by sensor interface circuitry (measuring circuit) 372,373,374 within the processing module 350. The sensor interface circuitry may include an amplifier and Wheatstone bridge configuration as shown in FIG. 1 or FIG. 2. Each sensor interface circuit 372,373,374 may be operatively connected to the processor 360. Each sensor interface circuit 372,373,374 may be capable of measuring the current (I) flowing through the associated thermal conductivity sensing element 416,417,418 and communicate the current (I) to the processor 360. The processor may communicate a voltage value (U) to each sensor interface circuit 472,473,474 which in response thereto applies the voltage as determined by the processor 360 to the associated thermal conductivity sensing element 416,417, 418.

The thermal conductivity sensing elements 416,417,418 may have a temperature-dependent electrical resistance, i.e. R=f(T). Consequently, the temperature of the thermal conductivity sensing elements 416,417,418 may be controlled by applying a variable voltage (U) to a sensing elements and measuring the current (I) flowing through the sensing element. In particular, the variable voltage (U) may be selected such that U=$R_{target}$* I, with $R_{target}$ being the resistance of the thermal conductivity sensor at a desired temperature ($T_{target}$). Each thermal conductivity sensing element may thus be operated at a predetermined temperature by regulating the voltage applied thereto.

The thermal conductivity sensing elements 416,417,418 may operate at three different temperatures. Alternatively, the outer thermal conductivity sensing elements 416, 417 may operate at a first temperature and the inner thermal conductivity sensing element 418 may operate at a higher second temperature. This configuration provides a beneficial symmetrical temperature distribution across the sensor. Also, when used in an environment with bidirectional airflow, the outer sensing elements operating at the same temperature may be used to determine the direction of airflow: The downstream sensing element is exposed to air that is at a higher temperature due to being pre-heated by the inner thermal conductivity sensing element 418. Consequently, less power is needed to maintain the first temperature of the downstream thermal conductivity sensing element than of the upstream thermal conductivity sensing element.

Figure 5:
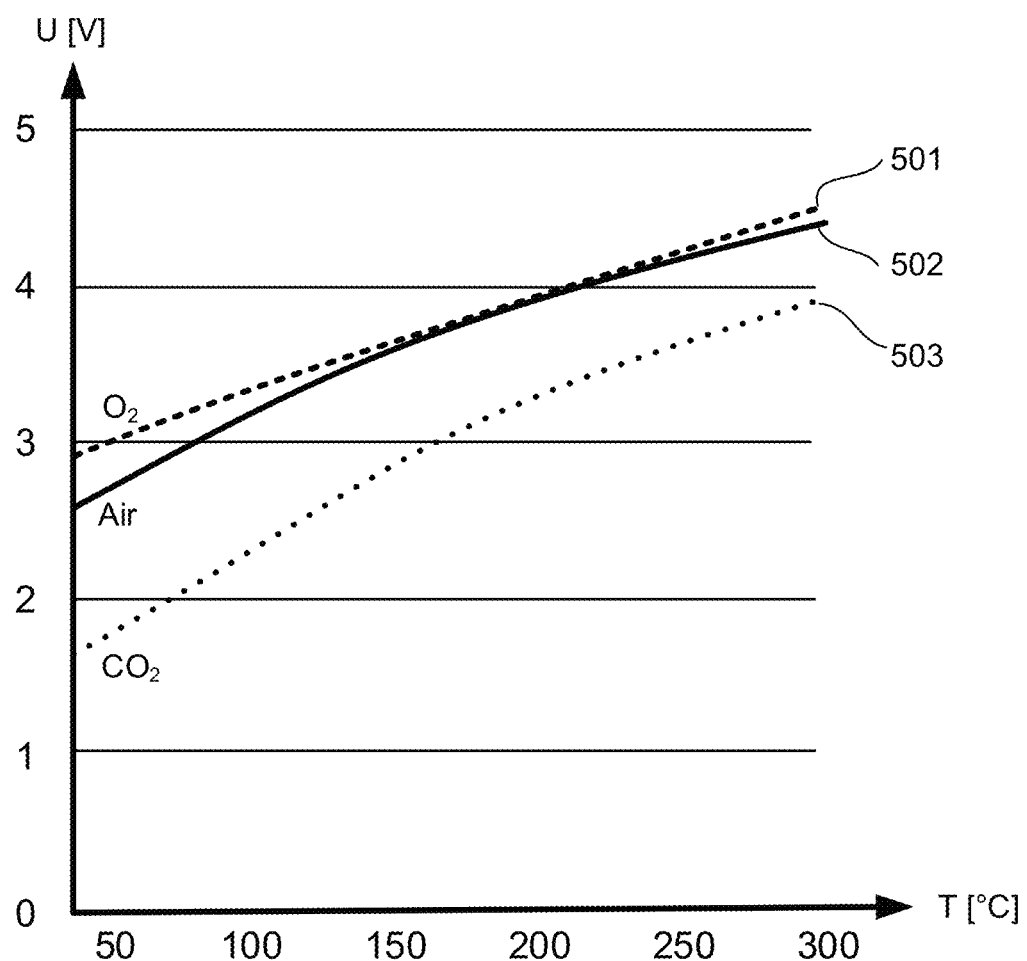
FIG. 5 is a plot showing the correlation of the temperature of a thermal conductivity sensing element and the voltage applied thereto when surrounded by different gases, the gas temperature being 20° C. without movement of the gas.

As shown in FIG. 5, the voltage U which is required to heat a thermal conductivity sensing element to a given temperature increases with the temperature of the thermal conductivity sensing element. Heating a thermal conductivity sensing element to a higher temperature requires a higher voltage. Independent of the gas which surrounds the thermal conductivity sensing element the curves 501,502,503 show that the voltage (U) increases with the temperature (T).

FIG. 5 also shows that the voltage which is required to maintain a given temperature of a thermal conductivity sensing element depends on the gas which surrounds the thermal conductivity sensing element. When the thermal conductivity sensing element is surrounded by oxygen (curve 501) or air (curve 502) a higher voltage is required than if the thermal conductivity sensing element is surrounded by carbon dioxide (curve 503). Oxygen is a better thermal conductor than carbon dioxide. Consequently, more heating power and thus a higher voltage is required to compensate for heat losses from the thermal conductivity sensing element into surrounding oxygen than into surrounding carbon dioxide. In this paper the voltage U that is required to maintain a particular temperature of the thermal conductivity sensing element is considered to be a measure of the thermal conductivity of the gas surrounding the sensing element. It should be understood that the voltage U also depends on the temperature of the gas surrounding the sensing element.

The thermal conductivity of a gas is largely independent of its pressure or density. The thermal conductivity of a gas does, however, depend on its temperature. The following table shows the thermal conductivity ($\lambda$) of various gases at different temperatures:

| Gas | $\lambda$[W/mK] @200 K | @250 K | @300 K | @400 K | @500 K |
| --- | --- | --- | --- | --- | --- |
| Air | 0.01836 | 0.02241 | 0.02623 | 0.03328 | 0.03971 |
| Carbon Dioxide | | 0.01295 | 0.01677 | 0.02515 | 0.03354 |
| Nitrogen | 0.0187 | | 0.0260 | 0.0326 | 0.0388 |
| Hydrogen | 0.1282 | 0.1561 | 0.182 | 0.228 | 0.272 |
| Oxygen | 0.01848 | 0.02244 | 0.02615 | 0.03324 | 0.04010 |
| Helium | 0.118 | 0.138 | 0.156 | 0.190 | 0.222 |
| Argon | 0.01245 | 0.01527 | 0.01787 | 0.02256 | 0.02675 |

The temperature-dependency of a gas's thermal conductivity can be use to infer the composition of an unknown gas which surrounds a thermal conductivity sensing element. A method for measuring gas properties may therefore heat a thermal conductivity sensing element to a predetermined temperature, measure the voltage that is necessary to maintain the predetermined temperature, and infer the composition of the gas surrounding the thermal conductivity sensing element.

Figure 6:
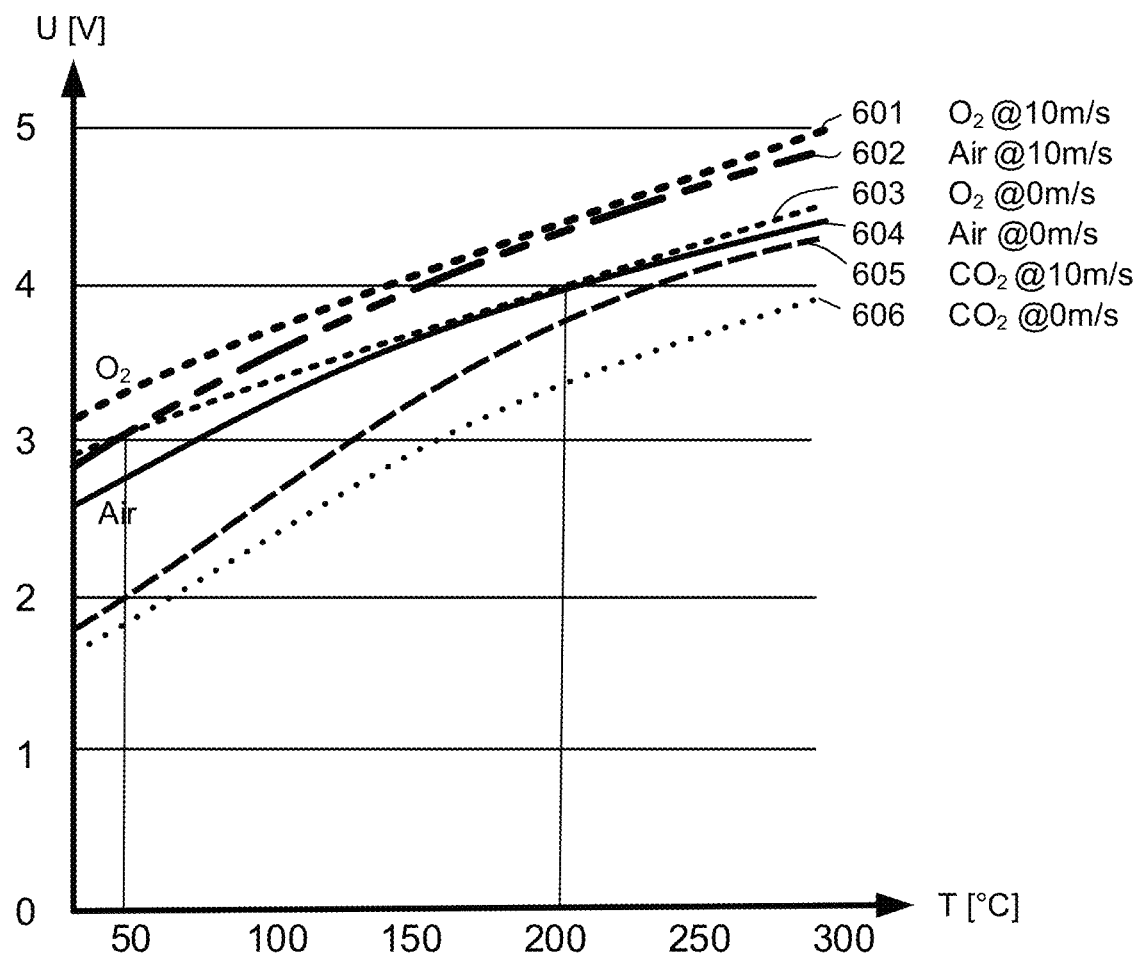
FIG. 6 is a plot showing the correlation of the temperature of a thermal conductivity sensing element and the voltage applied thereto when surrounded by different gases, the gas temperature being 20° C., with and without movement of the gas.

In practice, measuring thermal conductivity of a gas at a single temperature is insufficient to determine the composition thereof. As illustrated in FIG. 6, the voltage necessary to maintain a predetermined temperature of the thermal conductivity sensing element depends on the temperature of the sensing element, on the composition of the surrounding gas, and on the rate at which the gas is flowing past the sensing element. For example, if a voltage of 4V is necessary to maintain a 200° C. operating temperature of the thermal conductivity sensing element, the sensing element might be surrounded by pure oxygen which is not moving or by a mixture of oxygen and carbon dioxide moving at 10 m/s past the sensor. Therefore, to determine the composition of gas surrounding a thermal conductivity sensor, a single thermal conductivity sensing element may be operated at different temperatures over time. Alternatively, more than one thermal conductivity sensing element may be used, with different thermal conductivity sensing elements simultaneously operating at different temperatures.

A single thermal conductivity sensing element may for example be operated at three different temperatures. First, the thermal conductivity sensing element may be operated at 100° C. and the voltage $U_{100}$ that is required to maintain the 100° C. operating temperature may be determined and stored in a processor. Next, the conductivity sensing element may be operated at 200° C. and the voltage $U_{200}$ that is required to maintain the 200° C. operating temperature may be determined and stored in the processor. Finally, the conductivity sensing element may be operated at 300° C. and the voltage $U_{300}$ that is required to maintain the 300° C. operating temperature may be determined and stored in the processor.

Alternatively, a thermal conductivity sensor may comprise a first thermal conductivity sensing element 416, a second thermal conductivity sensing element 417, and a third thermal conductivity sensing element 418. The first thermal conductivity sensing element 416 may operate at a first predetermined temperature, e.g. 100° C. The second thermal conductivity sensing element 417 may operate at a second predetermined temperature, e.g. 200° C. Lastly, the third thermal conductivity sensing element 418 may operate at a third predetermined temperature, e.g. 300° C.

The processor 130,360 may determine the composition and/or the rate of gas flowing through the tube in response to the values $U_{100}$, $U_{200}$ and $U_{300}$. The processor may determine the composition and/or rate of gas through lookup tables that are stored in a memory component 133.

When used in spiroergometry, the processor may determine the amount of carbon dioxide in exhaled air and the total volume and/or mass of air that is passing through a tube. The processor may determine the direction of air flow to distinguish between inhaled and exhaled air.

A thermal conductivity sensor 405 that uses two or more thermal conductivity sensing element 416,417,418 which are simultaneously operating a different temperatures has some inherent advantages over a single thermal conductivity sensing element 211 which is operated at different temperatures over time. Primarily, the multi-element sensor 110,405 has better dynamic behavior, avoiding the delay that is inherent to a single-element sensor 210 which requires time for heating and cooling the sensing element 211 to different temperatures. The thermal conductivity sensing elements 416,417,418 in a multi-element sensor 405 may preferably be arranged close to each other so that the sensing elements are thermally coupled to each other, thereby reducing the overall power requirements for the sensor 405. Reduced power consumption is particularly advantageous when the sensor is used in battery-powered, mobile devices.

Within a multi-sensing element sensor 405 the third thermal conductivity sensing element 418 may be arranged centrally between the first thermal conductivity sensing element 416 and the second thermal conductivity sensing element 417. In such an arrangement the centrally arranged third thermal conductivity sensing element 418 is preferably operated at the highest temperature of the three sensing elements. The thermal conductivity sensing elements 416, 417 that are arranged on the outside are operated at lower temperatures, thereby reducing the overall power consumption of the sensor 405.

Various uses of the disclosed sensor and method for measuring gas properties are envisioned. In the field of spiroergometry systems, the sensor 405 may for example be used within a breathing mask that a person can wear while exercising. In the medical field, the sensor and method may be applied to monitoring the flow and composition of air with an anesthetic gas during surgery. The sensor and method may be used beyond the medical field, e.g. in industrial or consumer applications.

Both the single-sensing element variant and the multi-sensing element variant of the thermal conductivity sensor can measure the gas mass flow and the gas composition of air or another mixture of gases. The method can be used to derive a gas volume flow from the gas mass flow, even if the gas changes its composition during the measurement. This is necessary since different gases occupy a different volume with the same mass. In medical technology, for example, the same sensor can then be used to calculate the volume of air during inspiration and during expiration, even though the $CO_2$ content is significantly higher during expiration than during inspiration. That is, even though the mass flow of air during inspiration and expiration may be different, the correct volume flow can be derived by considering the measured increase in $CO_2$ in the exhaled air.

The operating principle of the sensor is based on hot-wire anemometry: An electrical conductor (wire, hot wire) is heated during hot wire anemometry. If a colder gas flows past the heated conductor, the conductor is either cooled or requires more power to maintain the same temperature. The heated conductor may be operated at a predetermined temperature by adjusting the power that is applied to the conductor. The power may be adjusted by controlling the voltage applied to the conductor through a variable voltage source. Alternatively, the power applied to the heated conductor may be kept constant, and the wire's temperature may be determined by measuring its resistance. The power required to maintain a constant temperature of the wire depends on the mass flow of gas passing by the wire.

The thermal conductivity sensing elements 416,417,418 may operate at predetermined absolute temperatures, e.g. 120° C., 220° C., and 320° C. Alternatively, the thermal conductivity sensing elements 416,417,418 may operate at a predetermined temperature difference above the temperature of the gas that is to be analyzed. Utilizing the temperature sensing elements 413, 414 the processor 360 may determine the temperature $T_{gas}$ of gas 408 inside the tube 401. The processor 360 may then select a target temperature of the thermal conductivity sensing elements 416,417,418 by applying a predetermined temperature differential $\Delta T$ to the temperature of the gas. For example, the processor 360 may select the target temperature of the thermal conductivity sensing elements 416,417,418 to be 100° C., 200° C. and 300° C. above the temperature of the gas 408.

In yet another variation the processor may apply predetermined amounts of heating power to the different thermal conductivity sensing elements 416,417,418, which will then assume a variable temperature above the temperature of the gas 408 within the tube 401.

It is possible to measure a gas concentration by measuring its thermal conductivity. Gases (e.g. $CO_2$) or gas mixtures (e.g. air) have specific thermal conductivities at given gas (air) temperatures. Thermal conductivity sensing elements 416,417,418 can be used to determine the thermal conductivity of a gas. The amount of heat that is transferred from the thermal conductivity sensing elements 416,417,418 into the gas depends on the gas's temperature, the gas's heat capacity, the interfacial thermal resistance between the sensing elements and the gas, and other properties of the gas or the sensor. The concentration of one or more gases within an unknown mixture of gases may thus be inferred by observing the thermal conductivity of the unknown mixture of gases at different temperatures and comparing the observed thermal conductivities with the thermal conductivities of gases with known composition at the same temperatures.

The electrical resistance of a heated wire increases with the temperature of the wire. Consequently, the voltage applied to the heated wire is correlated to the output power. In the following description the voltage applied to the heated wire is used to indicate the power which is consumed by the heated wire, given the known relationship of the wire's resistance and temperature. The processing module 120 regulates the hot wire by applying a variable voltage so that the wire maintains the desired temperature (resistance). The voltage required to maintain a given wire temperature is thus a measure of the heat transfer, the heat capacity and other properties of the gas since the resistance of the wire is kept constant by the processing module 120. The output power of the wire is $P=U^2/R$.

FIG. 5 shows that the voltage at the wire depends on the selected sensor temperature and on the composition of the gas. For each gas there is a defined temperature range. At the same sensor temperature, the voltage for each gas mixture is constant and thus unambiguous. More specifically, FIG. 5 shows the relationship of the voltage U [V] over the sensor temperature in degrees Celsius with different gases. The gas temperature here is 20 degrees Celsius. Each gas composition shows a different curve 501, 502, 503. This is a form of temperature spectroscopy. If the sensor temperature is known, the type of gas can be determined. The prerequisite for this is that it is precisely known which gas mixture components can change. This is often sufficient for biomedical applications because the application only considers a change in the CO2 or oxygen content.

Depending on the gas composition, the thermal conductivity sensing elements require different amount of power to maintain their target temperatures. The gas mass flow past the sensing elements also carries energy away from the sensor. The question therefore arises as to whether the sensor voltage reacts to a change in the gas mass flow or to a change in the gas composition. This question can be answerd by operating the sensors at two different temperatures.

Referring to FIG. 6, we assume that a voltage of 3.0 volts is applied to a sensing element to reach an operating temperature of 50 degrees Celsius above the temperature of the surrounding gas. This might indicate that the sensing element is surrounded by pure oxygen (without any movement) or flowing air at a speed of 10 meters per second. Further combinations would be conceivable, for example, that it is very fast (more than 10 meters per second) flowing CO2. If, however, a second sensing element is used which operates at 300 degrees Celsius above the temperature of the gas, pure oxygen will require a voltage of 4.5 volts to be applied to the second sensing element while air at a flow rate of 10 m/s will require a voltage of 4.8 volts to be applied to the second sensing element.

Preferably, several sensing elements 416,417,418 are disposed on a membrane 415 and operated at different temperatures in order to increase the accuracy and dynamic behavior of the sensor 405. This allows the simultaneous determination of mass flow and composition of a gas. For example, the mass flow of air and the concentration of $CO_2$ in air can be simultaneously measured with a multi-sensing-element sensor 405.

A multi-sensing element sensor 405 will use at least two sensing elements operating at two different temperatures, but may have more than two sensing elements, each operating at a different temperature. For example, a multi-sensing element sensor 405 may utilize three, four, five or six sensing elements. More generally speaking, a sensor 405 may utilize n sensing elements operating at n temperatures.

One method for measuring the thermal conductivity of a gas is the determination of how much power can be delivered to the gas from a heating element. The power required to maintain a set temperature of a heating element is positively correlated with the thermal conductivity of the surrounding gas. A reduction in the power required to maintain the heater temperature indicates a reduced thermal conductivity of the surrounding gas. This method can be used, if the temperature of the gas to be analyzed remains constant. If the temperature of the gas around the heating element is not constant, a method for compensating for a changing ambient temperature is needed.

A first method may use a static operating temperature, measure temperature of the gas, and mathematically correct the measured value. In this method, a heating element is maintained at a constant operating temperature independent of ambient temperature. The ambient temperature of the gas to be analyzed is measured by a separate independent temperature sensor. The ambient temperature can subsequently be used to mathematically correct the measured value based on the power absorbed by the sensor.

In an alternative second method the influence of ambient temperature can be eliminated by varying the operating temperature of the sensor. For this purpose, the sensor is not kept at a constant operating temperature, as described above, but is varied as a function of the ambient temperature. That is, the warmer the gas to be analyzed, the hotter the operating temperature of the thermal conductivity sensor. In this case the difference between the operating temperature and the ambient temperature may be kept constant. The power introduced into the sensor can thus be used directly for a measurement of the thermal conductivity of the gas.

Thermal conductivity measurements may utilize different sensing element temperatures with consideration of temperature-dependent thermal conductivity. A predetermined constant operating temperature of the sensing element may be used, the temperature of the gas may be measured and the measured value may be mathematically corrected. The mathematical correction takes into account that the thermal conductivity changes with the temperature. In practice, the calculation may utilize lookup-tables. The temperature-dependent thermal conductivity may automatically be taken into account by calibrating the sensor system at different temperatures to the different gas concentrations.

Alternatively, the temperature difference between the operating temperature of the sensing element and the ambient temperature of the surrounding gas may be kept constant. Thus, changes in the measured power required by the heating element to maintain this temperature difference depend solely on the change in concentration of the gas to be examined. In contrast to the above-described case, where the measured power can now be used alone for determining the thermal conductivity, the modified thermal conductivity is taken into account in this case by calibrating the system at different ambient temperatures. By means of an independent temperature sensor for measuring the gas temperature, the measured power can be assigned to the corresponding thermal conductivity at the same gas temperature.

For example, to measure the $CO_2$ concentration in air, a first sensing element may be operated at 50° C. above the air temperature and the second sensor may be operated at 200° C. above air temperature. If this delta-temperature is compensated to the extent that the required power of the heater remains the same at the same $CO_2$ concentration, the two sensors will always have the same output signal if the $CO_2$ concentration remains the same. If, however, $CO_2$ concentration in the air changes, the two output signals will differ.

To achieve more accurate measurements, a sensor may utilize not only two sensing elements at different delta-temperatures but a number of n sensing elements operating at n different delta temperatures. Thereby, a spectroscopy on the conductivity of the gases can be performed and the gas composition can be spectroscopically determined. As before, the sensing elements may operate at predetermined constant absolute temperatures or at predetermined delta temperatures above the ambient temperature of the gas that is to be analyzed.

To achieve even more accurate measurements of the $CO_2$ concentration in air it is desirable to eliminate the influence of air movement while the air is being analyzed. The second branch 303 of the tube 301 as shown in FIG. 3 utilizes two flaps 306, 307 which can be selectively closed such that air can no longer flow through the second branch 303 of tube 301. It is for example possible to open the flaps 306, 307 during exhaling and close them during inhaling. Exhaled air is thus trapped between the entry flap 306 and the exit flap 307 and can be accurately analyzed without having to account for the influence of air movement on the power required to maintain a particular sensing element's temperature. In this operating mode it is sufficient to determine the volume of air flowing through the tube 301 during inhaling, since the exhaled volume must equal the inhaled volume over longer time periods.

The disclosed method measures the thermal conductivity of gases by determining the power that can be delivered into the gas by a heating element. The method may use a heating element which is maintained at a constant absolute temperature and the power required for it is a measure of thermal conductivity. For this method to function at different gas temperatures, a constant, absolute temperature is not used, but a constant overtemperature, i.e. a constant temperature difference between the gas temperature and the temperature of the heating element, is applied. Thus, the applied power can be correlated to the thermal conductivity. To infer from the thermal conductivity to the gas composition, it is assumed that the same power is necessary to heat a heating element by relative e.g. 20 degrees Celsius. However, this assumption is not always correct, since the thermal conductivity of a gas is not the same at all temperatures. This knowledge can be used in two ways.

Either, one complicates the relative temperature control in such a way that it adjusts to a slightly adjusted (compensated) relative temperature. This is selected in such a way that the relative temperature is adjusted so as to compensate for the deviation of the change in the thermal conductivity over the temperature of the gas to be measured. $\Delta T$=const (relative temperature of the heater)

$$(T_{heater} - T_{gas}) = \Delta T$$

If the thermal conductivity coefficient change over the temperature is not to be taken into account one may assume $T_{compensation} = 0$. Otherwise, $T_{compensation}$ is the temperature which must be subtracted or added to $\Delta T$ so that the same power is used at the same gas concentration even though the coefficient of thermal conductivity changes due to a change in the gas temperature:

$$\Delta T - T_{compensation} = \Delta T_{compensated}$$

In the case of several overtemperatures, one measures the thermal conductivity coefficient of gases in different temperature dependence in order to increase the selectivity of the sensor system. For this purpose, one can use several sensors and operate them at different overtemperatures, or one uses a sensor at different temperatures over time.

The smaller the heating element, the faster the sensor system reacts to changes in the gas concentration. An arrangement of the sensors on a circular envelope 422 (envelope circle) leads to the best result. Leaking heat via the contact points or the carrier medium of the heater can lead to the outflow of energy levels which are not related to the gas concentration. For this reason, the sensors should be very small and the electrical feed 412 should be designed in such a way that as little heat as possible is dissipated through them. Preferably, the membrane 415 should have more than twice the diameter as the imaginary enveloping circle 422. The diaphragm distance 421 to the enveloping circle 422 should also have at least half the diameter of the imaginary enveloping circle 422. The classic design is a thin wire, which is stretched on two thin contact needles. A further structure is the planar construction in which a thin-film structure of nickel, platinum, molybdenum, etc. is applied in the form of a heating coil, spiral-shaped or meander-shaped, etc., on a substrate such as glass, ceramic, silicon, polyimide, plastic etc.

Figure 7:
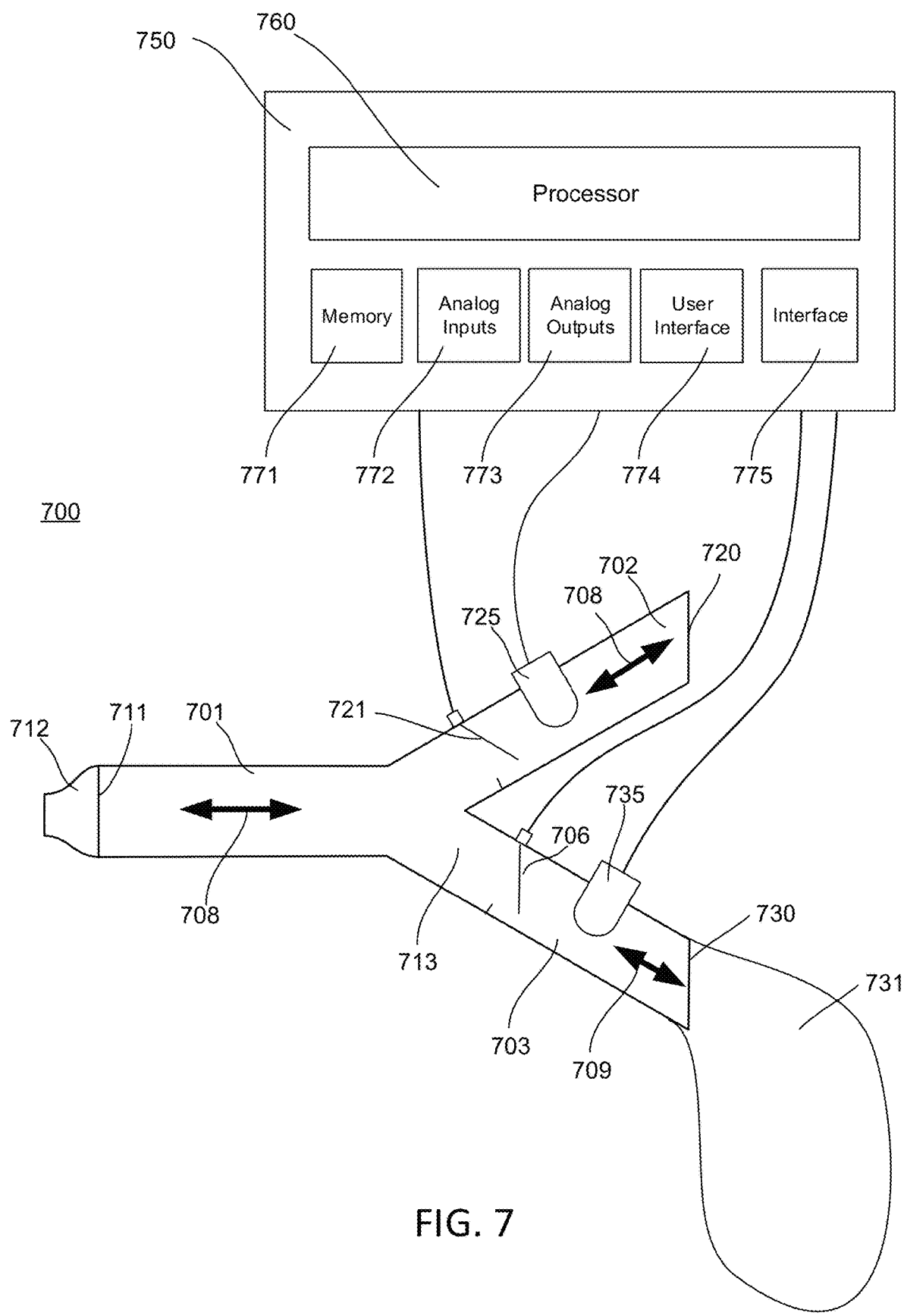
FIG. 7 is a schematic illustration of a breathing training device.

An alternative application in which the sensor may be advantageously used is a breathing training device 700 as shown in FIG. 7. The breathing training device 700 may be used for respiratory muscle training and enable a patient to better control his or her breathing. The breathing training device 700 may, for example, be used with patients suffering from chronic obstructive pulmonary disease (COPD).COPD is a type of obstructive lung disease characterized by long-term poor airflow. The main symptoms include shortness of breath and cough with sputum production. Breathing training, i.e. the targeted strengthening of the respiratory muscular system, has been found to be an effective treatment option for COPD, leading to significant improvement of patient's stamina and quality of life without the use of cortisone drugs.

The breathing training device 700 contains a mouthpiece 712 which is attached to a proximal end 711 of a tube 701. The tube 701 forms the body of the breathing training device 700. The tube 701 branches into a first branch 702 and a second branch 703. The breathing device 700 may be connected to a processing module 750. The processing module 750 may be integral to the breathing training device 700.

A distal end 720 of the first branch may be open. A first flow control valve 721 may be provided in the first branch 702 of the breathing training device 700 and operatively connected to the processing module 750. A first thermal conductivity sensor 725 may be provided in the first branch 702 of the breathing training device 700. The first thermal conductivity sensor 725 may be operatively connected to the processing module 750. By reading the first thermal conductivity sensor 725 the processing module 750 may determine the oxygen and carbon dioxide concentration of air flowing through the first branch 702.

A second thermal conductivity sensor 735 may be provided in the second branch 703 of the breathing training device 700. The second sensor 735 may be operatively connected to the processing module 750. By reading the second sensor 735 the processing module 750 may determine the oxygen and carbon dioxide concentration of air flowing through the second branch 703. The first sensor 725 and the second sensor 735 may comprise thermal conductivity sensing elements as described before. The first sensor 725 and/or the second sensor 735 may additionally comprise a pressure sensing element.

Installed at the distal end 730 of the second branch 703 may be an elastic bag or reservoir 731. A second flow control valve 706 may be arranged at an inlet (proximal) end 713 of the second branch 703.

While in use, the first flow control valve 721 and the second flow control valve 706 may be selectively adjusted between an open position and a closed position. The flow control valves 721,706 may be adjustable in multiple steps between the open position and the closed position, allowing for intermediate partially opened states in which air flow through the respective flow control valve is restricted, but not completely cut off. The flow control valves 721,706 may be selectively opened and closed in response to the pressure and/or flow of air through the first branch 702 and the second branch 703 as determined by the processing module 750 by reading the first thermal conductivity sensor 725 and the second thermal conductivity sensor 735. For example, in one particular operating condition the second flow control valve 706 may be completely closed, so that the second branch 703 is shut. The first flow control valve 721 may be partially opened to provide a desired resistance to inhaling and/or exhaling of air through the tube 701 and the first branch 702 as dictated by a training protocol that is programmed into a memory component 771 in the processing module 750.

The training protocol within processing module 750 may determine the opening and closing of flow control valves 721,706 in the breathing training device 700. The degree, to which the flow control valves 721,706 are opened, in turn determines the pneumatic resistance of air 708 flowing through the tube 701. The pneumatic resistance may be selectively adjusted separately during inhaling and exhaling. The pneumatic resistance during inhaling and exhaling may be selected based on previously conducted tests, and selectively adjusted through a user interface. The pneumatic resistance may be configured to change over the course of an exercise. Data related to air flow and concentration of oxygen and carbon dioxide over time may be stored in a non-volatile memory component 771 in the processing module 750 for further analysis.

During use, a patient may start breathing heavier than usual, and begin hyperventilating. Hyperventilation occurs when the rate and quantity of alveolar ventilation of carbon dioxide exceeds the body's production of carbon dioxide. Hyperventilation may cause physical symptoms such as dizziness, tingling in the lips, hands or feet, headache, weakness, fainting and seizures. In extreme cases it can cause carpopedal spasms (flapping and contraction of the hands and feet). By monitoring the concentration of oxygen and volume of inhaled air, through use of the first thermal conductivity sensor 725, the processing module 750 can recognize this condition, and actively prevent it. To prevent hyperventilation the processing module 750 may open the second branch 703 by selectively adjusting the second flow control valve 706, so that at least a part of the patient's exhaled air is captured in the elastic reservoir 731. The exhaled air in reservoir 731 contains significantly more carbon dioxide than normal air. The concentration of carbon dioxide in the exhaled air can be determined through the second thermal conductivity sensor 735. While the patient is inhaling the processing module 750 may open, at least partially, the second branch 703 so that the patient inhales a mixture of fresh air 708 through the first branch 702 and previously exhaled air 709 through the second branch 703. By using the flow measuring capability of the first sensor 725 and the second sensor 735 the processing module 750 can adjust the concentration and/or volume of carbon dioxide that the patient inhales and actively prevent hyperventilation.

The processing module 750 may comprise a processor 760 which is operatively connected to a memory 771, analog inputs 772, analog outputs 773, a user interface 774 and an external interface 775.

Exemplary Embodiments

A sensing system for measuring a gas property, comprising:
a thermal conductivity sensing element disposed within a mixture of gases; and
a processing module operatively connected to the thermal conductivity sensing element,
wherein the processing module applies power to alternately heat the thermal conductivity sensing element to a first temperature and to a second temperature which is different than the first temperature and
wherein the processing module measures a first thermal conductivity of the mixture of gases while the thermal conductivity sensing elements is heated to the first temperature and
wherein the processing module measures a second thermal conductivity of the mixture of gases while the thermal conductivity sensing element is heated to the second temperature and
wherein the processing module determines a concentration of a first gas within the mixture of gases in response to the measured first thermal conductivity and the measured second thermal conductivity.

A sensing system for measuring a gas property, comprising:
a first thermal conductivity sensing element disposed within a mixture of gases; a second thermal conductivity sensing element disposed within the mixture of gases; and
a processing module operatively connected to the first thermal conductivity sensing element and to the second thermal conductivity sensing element,
wherein the processing module measures a first thermal conductivity of the mixture of gases while the first thermal conductivity sensing element is heated to a first operating temperature and
wherein the processing module measures a second thermal conductivity of the mixture of gases while the second thermal conductivity sensing element is heated to a second operating temperature and
wherein the processing module determines a concentration of a first gas within the mixture of gases in response to the measured first thermal conductivity and the measured second thermal conductivity.

A device for analyzing a breathing gas, comprising:
a first thermal conductivity sensing element disposed within the breathing gas, the first thermal conductivity sensing element being operatively connected to a processing module,
wherein the processing module measures a first thermal conductivity of breathing gas flow while the first thermal conductivity sensing element is heated to a first operating temperature and
wherein the processing module measures a second thermal conductivity of the breathing gas flow while the first thermal conductivity sensing element is heated to a second operating temperature and
wherein the processing module determines a concentration of carbon dioxide within the breathing gas flow in response to the measured first thermal conductivity and the measured second thermal conductivity.

A breathing training apparatus, comprising:
a tube having a proximal end connected to a breathing mask and a distal end connected to a splitter;
a first branch having a proximal end connected to the splitter and an open distal end; a first thermal conductivity sensing element arranged within the first branch and operatively connected to a processing module;
a first flow control valve arranged in the first branch and operatively connected to the processing module;
a second branch having a proximal end connected to the splitter and a distal end connected to an inflatable reservoir;
a second thermal conductivity sensing element arranged within the second branch and operatively connected to a processing module;
a second flow control valve arranged in the second branch and operatively connected to the processing module.

The breathing training apparatus as above,
wherein the control apparatus determines a concentration of carbon dioxide in exhaled air flowing through the tube and
controls the first flow control valve to reduce the flow of air through the first branch and
controls the second flow control valve to increase the flow of air through the second branch.

A method for measuring a property of a mixture of gases, comprising:
providing one or more thermal conductivity sensing elements within the mixture of gases;
applying heating power to one of the one or more thermal conductivity sensing elements and controlling the heating power to maintain a selected first temperature;
measuring a first voltage and/or first power required to maintain the first temperature;
applying heating power to one of the one or more thermal conductivity sensing elements and controlling the heating power to maintain a selected second temperature;
measuring a second voltage and/or second power required to maintain the second temperature;
determining the concentration of at least one gas contained in the mixture of gases in response to the measured first voltage and/or first power and the measured second voltage and/or second power.

While the present invention has been described with reference to exemplary embodiments, it will be readily apparent to those skilled in the art that the invention is not limited to the disclosed or illustrated embodiments but, on the contrary, is intended to cover numerous other modifications, substitutions, variations and broad equivalent arrangements that are included within the spirit and scope of the following claims.

What is claimed is:

1. A respiratory gas sensing system, comprising:
a thermal conductivity sensor disposed within a respiratory flow path including
a first thermal conductivity sensing element comprising a first meander-shaped resistive wire having a plurality of first turns and
a second thermal conductivity sensing element comprising a second meander-shaped resistive wire having a plurality of second turns,
the first turns and the second turns being arranged adjacent to a common enveloping circle; and
a processing module operatively connected to the thermal conductivity sensor,
wherein the processing module measures a first thermal conductivity of a respiratory gas by operating the first thermal conductivity sensing element at a first temperature and
wherein the processing module measures a second thermal conductivity of the respiratory gas by operating the second thermal conductivity sensing element at a second temperature, the second temperature being higher than the first temperature, and wherein operating the conductivity sensing elements includes applying electric power thereto and determining a voltage associated with the electric power required to maintain the respective temperature, and wherein the processing module determines a concentration of carbon dioxide within the respiratory gas in response to the measured first thermal conductivity and the measured second thermal conductivity.

2. The respiratory gas sensing system as in claim 1, wherein the first thermal conductivity sensing element and the second thermal conductivity sensing element are arranged within a tube through which the respiratory gas flows, and wherein the first thermal conductivity sensing element and the second thermal conductivity sensing element are arranged in a plane substantially parallel to a longitudinal extension of the tube.

3. The respiratory gas sensing system as in claim 1, wherein the first thermal conductivity sensing element is part of a first Wheatstone bridge measuring circuit and wherein the second thermal conductivity sensing element is part of a second Wheatstone bridge measuring circuit.

4. The respiratory gas sensing system as in claim 1, wherein the first and the second thermal conductivity sensing elements are arranged on a membrane within an area of less than 4 $mm^2$.

5. The respiratory gas sensing system as in claim 1, wherein the processing module comprises a memory having data stored in a lookup-table and wherein the processing module determines the concentration of carbon dioxide by reference to the lookup-table, wherein the lookup-table comprises predetermined values associating the concentration of carbon dioxide with thermal conductivity measurements.

6. The respiratory gas sensing system as in claim 1, wherein the thermal conductivity sensor further comprises:

a third thermal conductivity sensing element, and wherein the processing module is configured to operate the third thermal conductivity sensing element at a third temperature, the third temperature being higher than the second temperature.

7. The respiratory gas sensing system as in claim 6, wherein the third thermal conductivity sensing element is arranged centrally between the first thermal conductivity sensing element and the second thermal conductivity sensing element.

8. The respiratory gas sensing system as in claim 1, wherein the first temperature and the second temperature are predetermined absolute temperatures.

9. The respiratory gas sensing system as in claim 1, wherein the first temperature is selected in response to measuring a temperature of the respiratory gas.

10. A spiroergometer, comprising:

a tube having a proximal end and a distal end;

a breathing mask connected to the proximal end of the tube; and the respiratory gas sensing system as in claim 1, wherein the thermal conductivity sensor is arranged within the tube.

11. The spiroergometer as in claim 10, wherein the breathing mask and the respiratory gas sensing system are formed as a portable, battery powered device which is worn by a subject while exercising.

12. The spiroergometer as in claim 10, wherein the tube comprises a first branch and a second branch and wherein a trap section for exhaled respiratory gas is formed between two flow control valves in the second branch, and wherein the thermal conductivity sensor is arranged within the trap section of the second branch.

13. A battery-powered mobile device comprising the respiratory gas sensing system as in claim 1.

14. A respiratory gas sensing system, comprising:

a thermal conductivity sensor disposed within a respiratory flow path; and a processing module operatively connected to the thermal conductivity sensor, wherein the thermal conductivity sensor comprises:

two outer thermal conductivity sensing elements, each comprising a first meander-shaped resistive wire having a plurality of first turns; and an inner thermal conductivity sensing element arranged between the two outer thermal conductivity sensing elements comprising a second meander-shaped resistive wire having a plurality of second turns, the first turns and the second turns being arranged adjacent to a common enveloping circle; and wherein the processing module measures a first thermal conductivity of a respiratory gas by operating the two outer thermal conductivity sensing elements at a first temperature and wherein the processing module measures a second thermal conductivity of the respiratory gas by operating the inner thermal conductivity sensing element at a second temperature, the second temperature being higher than the first temperature, and wherein operating the conductivity sensing elements includes applying electric power thereto and determining a voltage associated with the electric power required to maintain the respective temperature, and wherein the processing module determines a concentration of carbon dioxide within the respiratory gas in response to the measured first thermal conductivity and the measured second thermal conductivity.

15. The respiratory gas sensing system as in claim 14, wherein the two outer thermal conductivity sensing elements and the inner thermal conductivity sensing element are disposed on a membrane.

16. The respiratory gas sensing system as in claim 14, further comprising two temperature sensing elements, the two outer thermal conductivity sensing elements being arranged between the two temperature sensing elements.

17. The respiratory gas sensing system as in claim 14, wherein the two outer thermal conductivity sensing elements and the inner thermal conductivity sensing element are arranged within a tube through which the respiratory gas flows, and wherein the two outer thermal conductivity sensing elements and the inner thermal conductivity sensing element are arranged in a plane substantially parallel to a longitudinal extension of the tube.

18. The respiratory gas sensing system as in claim 14, further comprising a first temperature sensing element arranged upstream of the two outer thermal conductivity sensing elements and a second temperature sensing element arranged downstream of the two outer thermal conductivity sensing elements.

19. A battery-powered mobile device comprising the respiratory gas sensing system as in claim 14.

* * * * *